US009629752B1

(12) United States Patent
Graham

(10) Patent No.: US 9,629,752 B1
(45) Date of Patent: Apr. 25, 2017

(54) WELDING HELMET WITH A SENSOR-OPERATED LIGHT AND PHOTOCHROMIC VISOR LENS

(71) Applicant: James Graham, New Albany, IN (US)

(72) Inventor: James Graham, New Albany, IN (US)

( * ) Notice: Subject to any disclaimer, the term of this patent is extended or adjusted under 35 U.S.C. 154(b) by 183 days.

(21) Appl. No.: 14/686,122

(22) Filed: Apr. 14, 2015

(51) Int. Cl.
*A61K 9/06* (2006.01)
*B23K 31/02* (2006.01)
*A61F 9/06* (2006.01)

(52) U.S. Cl.
CPC .................. *A61F 9/067* (2013.01)

(58) Field of Classification Search
CPC .......... A61F 9/067; A61F 9/065; A61F 9/061; G02F 1/13306; G02F 1/13318; G02F 1/0126; G02F 1/1533; G02F 1/163; G02F 2001/13324; G02F 1/15; G02F 1/1523; G02F 2001/1515; G02F 2001/1519; B32B 17/10036; B32B 17/10174; G01J 1/44
USPC ....................................................... 219/147
See application file for complete search history.

(56) References Cited

U.S. PATENT DOCUMENTS

| | | | | |
|---|---|---|---|---|
| 4,155,122 A | * | 5/1979 | Budmiger | A61F 9/065 2/8.7 |
| 4,332,004 A | * | 5/1982 | Slaughter | F16P 1/06 2/10 |
| 6,429,733 B1 | | 8/2002 | Pagliolo et al. | |
| 7,161,116 B2 | | 1/2007 | Steinemann | |
| 7,534,005 B1 | | 5/2009 | Buckman | |
| 7,934,846 B1 | * | 5/2011 | Schwanz | F21L 4/04 362/103 |
| 8,721,103 B2 | * | 5/2014 | Robinson | A61F 9/064 362/105 |
| 2010/0223706 A1 | * | 9/2010 | Becker | A42B 3/30 2/8.2 |
| 2014/0007312 A1 | * | 1/2014 | Wright | A61F 9/064 2/8.2 |

* cited by examiner

*Primary Examiner* — Vy Nguyen
(74) *Attorney, Agent, or Firm* — Stevenson IP, LLC

(57) ABSTRACT

A welding helmet with a sensor-operated light and photochromic visor lens including a welding helmet body configured, sized, and shaped to cover and substantially conform to a welder's forehead. A frustoconical protrusion, integrated into a front side of the welding helmet body, houses a battery-operated LED light bulb. At least one photosensor is disposed proximal the protrusion. Upon the detection of a welding arc by the at least one photosensor, an auto-darkening filtered visor lens darkens and the LED light bulb in activated. A battery compartment, an on-off switch, and a microchip are disposed on a rear side of the welding helmet body. A padded length-adjustable strap is pivotally disposed across the rear side of the welding helmet body.

6 Claims, 3 Drawing Sheets

WELDING HELMET WITH A SENSOR-OPERATED LIGHT AND PHOTOCHROMIC VISOR LENS

CROSS-REFERENCE TO RELATED APPLICATIONS

Not Applicable

FEDERALLY SPONSORED RESEARCH OR DEVELOPMENT

Not Applicable

INCORPORATION BY REFERENCE OF MATERIAL SUBMITTED ON A COMPACT DISK

Not Applicable

BACKGROUND OF THE INVENTION

Various types of welding helmets with associated accessories are known in the prior art. One of known welding helmets includes a light emitting diode lamp that is controlled by an on-off power switch disposed with a rear chamber of the housing. However, what is needed is a welding helmet with an integrated sensor-operated light and photochromic visor lens.

FIELD OF THE INVENTION

The present invention relates to welding helmets, and more particularly, to a welding helmet with a sensor-operated light and photochromic visor lens.

SUMMARY OF THE INVENTION

The general purpose of the present welding helmet with a sensor-operated light and photochromic visor lens, described subsequently in greater detail, is to provide a welding helmet with a sensor-operated light and photochromic visor lens which has many novel features that result in a welding helmet with a sensor-operated light and photochromic visor lens which is not anticipated, rendered obvious, suggested, or even implied by prior art, either alone or in combination thereof.

To accomplish this, the present welding helmet with a sensor-operated light and photochromic visor lens includes a welding helmet body configured, sized, and shaped to cover and substantially conform to a welder's forehead. A frustoconical protrusion, integrated into a front side of the welding helmet body proximal a top side thereof, houses a battery-operated light emitting diode (LED) light bulb. At least one photosensor is disposed proximal the protrusion. A battery compartment, on-off switch, and microchip are disposed on a rear side of the welding helmet body. An auto-darkening filtered visor lens is centrally disposed in the front side of the welding helmet body. Upon the detection of the welding arc by the at least one photosensor, the visor lens darkens automatically and the light bulb is activated when the on-off switch is also in an "on" position. A length-adjustable strap is pivotally disposed across the rear side of the welding helmet body. A padded cushion is continuously disposed on an interior side of the strap.

Thus has been broadly outlined the more important features of the present welding helmet with a sensor-operated light and photochromic visor lens so that the detailed description thereof that follows may be better understood and in order that the present contribution to the art may be better appreciated.

BRIEF DESCRIPTION OF THE DRAWINGS

Figures

DETAILED DESCRIPTION OF THE DRAWINGS

Figure 1:
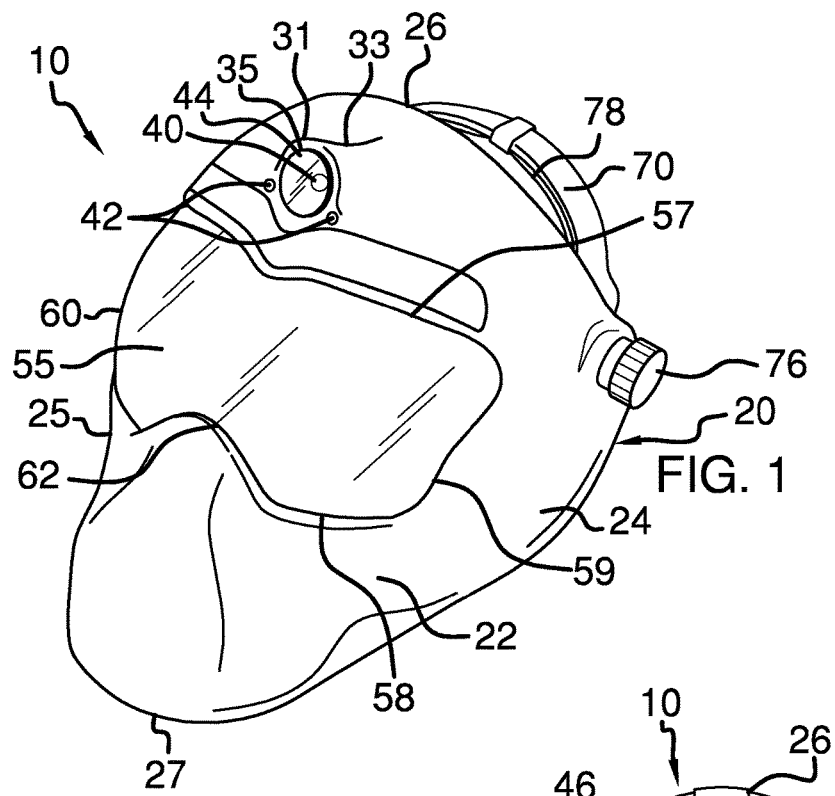
FIG. 1 is an isometric view.
Figure 2:
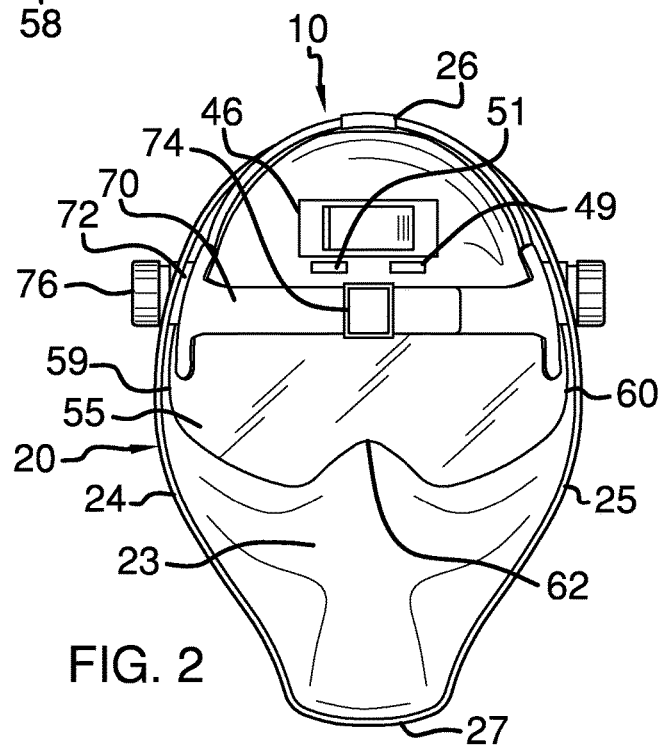
FIG. 2 is a rear elevation view.
Figure 3:
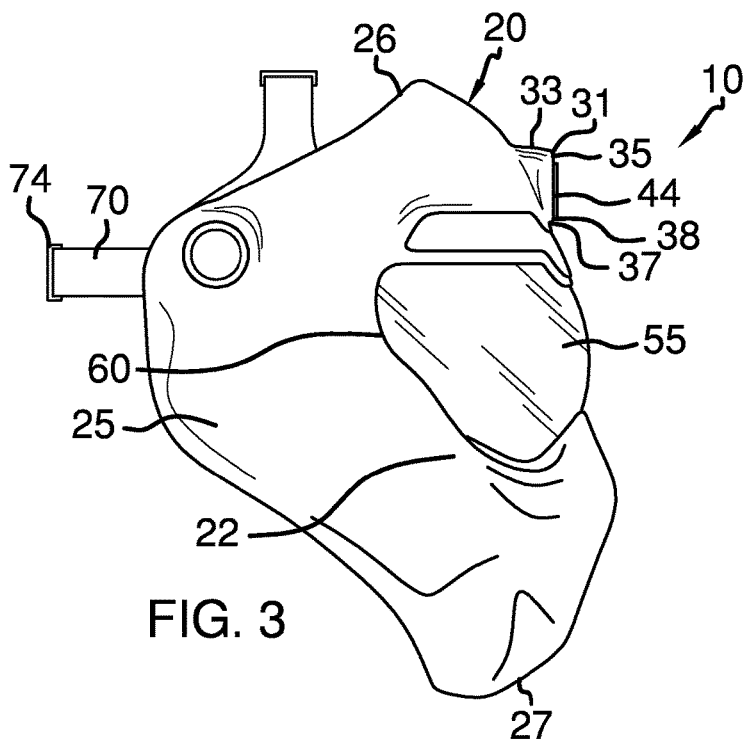
FIG. 3 is a side elevation view.
Figure 4:
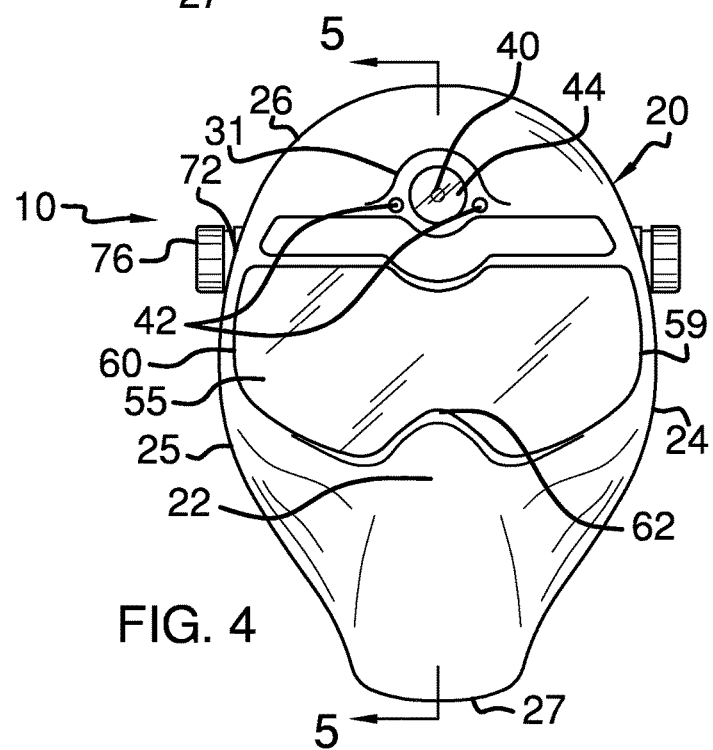
FIG. 4 is a front elevation view.
Figure 5:
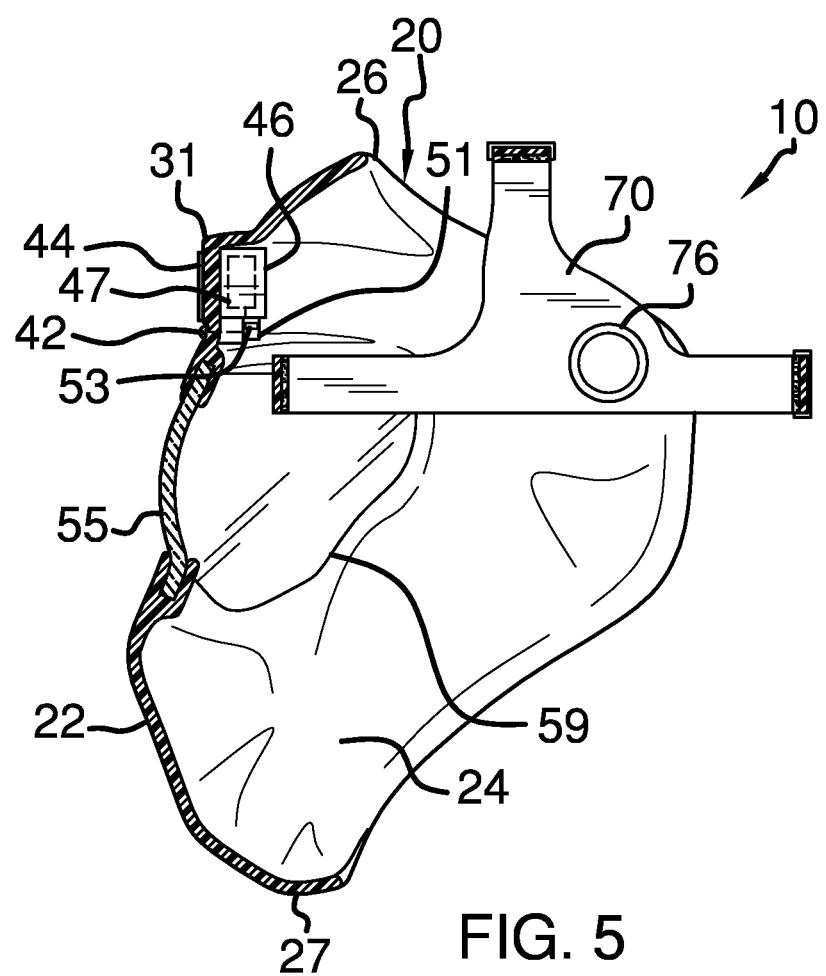
FIG. 5 is a cross-sectional view taken along line 5-5 of FIG. 4.

With reference now to the drawings, and in particular FIGS. 1 through 5 thereof, an example of the instant welding helmet with a sensor-operated light and photochromic visor lens employing the principles and concepts of the present welding helmet with a sensor-operated light and photochromic visor lens and generally designated by the reference number 10 will be described.

Referring to FIGS. 1 through 5 the present welding helmet with a sensor-operated light and photochromic visor lens 10 is illustrated. The welding helmet with a sensor-operated light and photochromic visor lens 10 includes a welding helmet body 20 having a front side 22, a rear side 23, a right side 24, a left side 25, a top side 26, and a bottom side 27. The welding helmet body 20 is configured, sized, and shaped to cover and substantially conform to a welder's forehead on the top side 26, cheekbones on the right and left sides 24, 25, eyes and nose in a central portion 28 of the welding helmet body 20, and chin on the bottom side 27.

A frustoconical protrusion 31 is integrated into the front side 22 in a central position proximal the top side 26. The protrusion 31 has an upper side 33 extending from the front side 22 at an angle in a range of 90 degrees to 145 degrees relative to the front side 22 proximal the top side 26. The protrusion 31 further has a forward side 35, and an L-shaped lower side 37 opposite the upper side 33 of the protrusion 31. The forward side 35 is disposed at a right angle relative to the upper side 33. The lower side 37 is directed from a bottom end 38 of the forward side 35 to the front side 22 of the welding helmet body 20.

A battery-operated light emitting diode (LED) light bulb 40 is integrated into the front side 22 of the welding helmet body 20 within the protrusion 31. At least one photosensor 42 is disposed on the front side 22 of the welding helmet body 20 proximal the protrusion 31. A heat-resistant transparent covering 44 is disposed over the forward side 35 of the protrusion 31 to protect the light bulb 40. The light bulb 40 is a light emitting diode to provide a bright light compared to other light bulb types which consume more battery power and requiring more space than the LED light bulb 40. The LED light bulb 40 reduces shadowing to provide a clear view of the area to be welded, even in a tight spot, to achieve a solid, stable weld. In turn, the LED light bulb 40 reduces a welder's time and energy required to achieve a solid, stable weld. The heat resistance of the covering 44 is provided to prevent the covering from melting during welding operations, while protecting the light bulb 40. The covering 44 is transparent to permit the maximum light produced by the light bulb 40 to penetrate through the covering 44. The transparent covering 44 can also be impact-resistant to prevent damage to the covering 44 from flying debris during use of the present device 10 while welding. The provision of more than one of the at least one photosensor 42 permits the photosensors 42 to detect a welding arc from different angles relative to the welding helmet body 20.

A battery compartment 46 is disposed on the rear side 23 of the welding helmet body 20 proximal the protrusion 31. The battery compartment 46 is configured to house at least one battery 47. An on-off switch 49 is disposed on the rear side 23 of the welding helmet body 20 proximal the battery compartment 46. A housing 51 is disposed on the rear side 23 of the welding helmet body 20 proximal the battery compartment 46 and the on-off switch 49. A microchip 53 is disposed within the housing 51. The microchip 53, the on-off switch 49, the at least one battery 47, the light bulb 40, and the at least one photosensor 42 are in operational communication with each other.

An auto-darkening filtered visor lens 55 is centrally disposed in the front side 22 of the welding helmet body 20. The visor lens 55 has an upper side 57, a lower side 58, a first side 59, and a second side 60 opposite the first side 59. Each of the first side 59 and the second side 60 is disposed proximal to the respective right side 24 and left side 25 of the welding helmet body 20. The visor lens 55 has a concave notch 62 centrally disposed in the lower side 58 thereof. The visor lens 55 is activated by the photosensor 42 to darken automatically upon detection by the at least one photosensor 42 of the welding arc. Upon the detection of the welding arc by the at least one photosensor 42, the visor lens 55 darkens automatically and the light bulb 40 is activated when the on-off switch 49 is also in an "on" position.

A length-adjustable strap 70 is disposed across the rear side 23 of the welding helmet body 20. The strap 70 has a pair of outer ends 72. The strap 70 extends from the right side 24 to the left side 25 proximal the upper side 57 of the visor lens 55. A buckle 74 slidingly engages the strap 70 to permit the adjustment of a length of the strap 70. A pair of strap pivot members 76 is provided with one of the strap pivot members 76 being disposed on each of the right and left sides 24, 25 of the welding helmet body 20. A padded cushion 78 is continuously disposed on an interior side 79 of the strap 70. The outer ends 72 of the strap 70 pivotally engage the pivot members 76 to permit the strap to be adjusted for the welder's comfort.

The present device 10 can include and, alternately, be limited to only the features, structure, and elements described and illustrated herein. The auto-darkened filtered visor lens 55 permits the welder to weld under a variety of welding operations that require different shades of protection and, further, permits the welder to keep the welding helmet body on at all times which, in turn, prevents neck strain often associated with trying to flip down a faceshield when striking the welding arc. The present auto-darkened filtered visor lens 55 can reduce the need for wearing secondary safety lenses behind the visor lens 55. The visor lens 55 can be impact-resistant. The welding helmet body 20 and the visor lens 55 can also be ANSI-compliant. Although the auto-darkened filtered visor lens 55 does not darken until the welding arc is struck, if the welding helmet body 20 and the visor lens 55 are ANSI-compliant, UV and IR rays will be blocked whether the helmet is on or off. The visor lens 55 can be configured to take a millisecond or less to change the auto-darkened shade.

What is claimed is:

1. A welding helmet with a sensor-operated light and photochromic visor lens comprising:

a welding helmet body having a front side, a rear side, a right side, a left side, a top side, and a bottom side, wherein the welding helmet body is configured, sized, and shaped to cover and generally conform to a welder's face;

a frustoconical protrusion integrated into the front side in a central position proximal the top side, the protrusion having an upper side extending from the front side at an angle in a range of 90 degrees to 145 degrees relative to the front side proximal the top side, the protrusion further having a forward side, and an L-shaped lower side opposite the upper side of the protrusion, the forward side disposed at a right angle relative to the upper side, the lower side directed from a lower end of the forward side to the front side of the welding helmet body;

a battery-operated light emitting diode light bulb integrated into the front side of the welding helmet body within the protrusion;

at least one photosensor disposed on the front side of the welding helmet body proximal the protrusion;

a transparent covering disposed over the forward side of the protrusion, wherein the transparent covering is configured to protect the light bulb;

a battery compartment disposed on the rear side of the welding helmet body proximal the protrusion, wherein the battery compartment is configured to house at least one battery;

an on-off switch disposed on the rear side of the welding helmet body proximal the battery compartment;

a housing disposed on the rear side of the welding helmet body proximal the battery compartment and the on-off switch;

a microchip disposed within the housing, the microchip, the on-off switch, the at least one battery, the light bulb, and the photosensor being in operational communication with each other;

an auto-darkening filtered visor lens centrally disposed in the front side of the welding helmet body, the visor lens having an upper side, a lower side, a first side, and a second side opposite the first side, each of the first side and the second side being disposed proximal to the respective right side and left side of the front side of the welding helmet body, the visor lens in operational communication with the at least one photosensor, wherein the visor lens darkens automatically upon detection by the at least one photosensor of a welding arc;

a length-adjustable strap disposed across the rear side of the welding helmet body, the strap having a pair of outer ends, the strap extending from the right side to the left side proximal the upper side of the visor lens;

wherein upon the detection of a welding arc by the at least one photosensor, the visor lens darkens automatically and the light bulb is activated when the on-off switch is also in an "on" position.

2. The welding helmet with a sensor-operated light and photochromic visor lens of claim 1 further comprising:

a pair of strap pivot members, one of the strap pivot members disposed on each of the right and left sides of the welding helmet body;

wherein the outer ends of the strap pivotally engage the pivot members.

3. The welding helmet with a sensor-operated light and photochromic visor lens of claim 2 further comprising a padded cushion continuously disposed on an interior side of the strap.

4. The welding helmet with a sensor-operated light and photochromic visor lens of claim 3 further wherein the visor lens is impact-resistant.

5. The welding helmet with a sensor-operated light and photochromic visor lens of claim 4 further wherein the visor lens is ANSI-compliant.

6. A welding helmet with a sensor-operated light and photochromic visor lens consisting of:
- a welding helmet body having a front side, a rear side, a right side, a left side, a top side, and a bottom side, wherein the welding helmet body is configured, sized, and shaped to cover and substantially conform to a welder's forehead on the top side, cheekbone on each of the right and left sides, eyes and nose in a central portion of the welding helmet body, and chin on the bottom side;
- a frustoconical protrusion integrated into the front side in a central position proximal the top side, the protrusion having an upper side extending from the front side at an angle in a range of 90 degrees to 145 degrees relative to the front side proximal the top side, the protrusion further having a forward side, and an L-shaped lower side opposite the upper side of the protrusion, the forward side disposed at a right angle relative to the upper side, the lower side directed from a lower end of the forward side to the front side of the welding helmet body;
- a battery-operated light emitting diode light bulb integrated into the front side of the welding helmet body within the protrusion;
- at least one photosensor disposed on the front side of the welding helmet body proximal the protrusion;
- a transparent covering disposed over the forward side of the protrusion, wherein the transparent covering is configured to protect the light bulb;
- a battery compartment disposed on the rear side of the welding helmet body proximal the protrusion, wherein the battery compartment is configured to house at least one battery;
- an on-off switch disposed on the rear side of the welding helmet body proximal the battery compartment;
- a housing disposed on the rear side of the welding helmet body proximal the battery compartment and the on-off switch;
- a microchip disposed within the housing, the microchip, the on-off switch, the at least one battery, the light bulb, and the photosensor being in operational communication with each other;
- an auto-darkening filtered visor lens centrally disposed in the front side of the welding helmet body, the visor lens having an upper side, a lower side, a first side, and a second side opposite the first side, each of the first side and the second side being disposed proximal to the respective right side and left side of the welding helmet body, the visor lens having a concave notch centrally disposed in the lower side thereof, the visor lens in operational communication with the at least one photosensor, wherein the visor lens darkens automatically upon detection by the at least one photosensor of a welding arc;
- a length-adjustable strap disposed across the rear side of the welding helmet body, the strap having a pair of outer ends, the strap extending from the right side to the left side proximal the upper side of the visor lens;
- a buckle disposed on the strap, wherein the buckle slidingly engages the strap, wherein the buckle is configured to permit the adjustment of a length of the strap;
- a pair of strap pivot members, one of the strap pivot members disposed on each of the right and left sides of the welding helmet body; and
- a padded cushion continuously disposed on an interior side of the strap;
- wherein the outer ends of the strap pivotally engage the pivot members; and
- wherein upon the detection of a welding arc by the at least one photosensor, the visor lens darkens automatically and the light bulb is activated when the on-off switch is also in an "on" position.

\* \* \* \* \*